(12) United States Patent
Manrique et al.

(10) Patent No.: US 10,751,111 B2
(45) Date of Patent: Aug. 25, 2020

(54) ELECTRO-SURGICAL BIPOLAR FORCEPS

(71) Applicant: INTEGRA LIFESCIENCES SWITZERLAND SÀRL, Le Locle (CH)

(72) Inventors: Lisette Manrique, Taunton, MA (US); John Buonanno, Bristol, RI (US)

(73) Assignee: INTEGRA LIFESCIENCES SWITZERLAND SARL, Le Locle (CH)

( * ) Notice: Subject to any disclaimer, the term of this patent is extended or adjusted under 35 U.S.C. 154(b) by 71 days.

(21) Appl. No.: 15/645,557

(22) Filed: Jul. 10, 2017

(65) Prior Publication Data
US 2017/0303994 A1   Oct. 26, 2017

Related U.S. Application Data

(63) Continuation of application No. 11/772,969, filed on Jul. 3, 2007, now abandoned.

(51) Int. Cl.
*A61B 18/14* (2006.01)

(52) U.S. Cl.
CPC .. *A61B 18/1442* (2013.01); *A61B 2018/1462* (2013.01); *A61B 2018/1495* (2013.01)

(58) Field of Classification Search
CPC ............ A61B 18/1442; A61B 18/1445; A61B 18/1447; A61B 2018/1452–1462; A61B 2018/00172; A61B 2018/00178; A61B 17/282; A61B 2017/2931
See application file for complete search history.

(56) References Cited

U.S. PATENT DOCUMENTS

| | | | | |
|---|---|---|---|---|
| 3,685,518 A * | 8/1972 | Beuerle | .................. | A61B 17/30 606/51 |
| 5,662,647 A * | 9/1997 | Crow | .................... | A61B 18/14 606/41 |
| 6,090,107 A * | 7/2000 | Borgmeier | ............. | A61B 18/14 606/41 |
| 6,298,550 B1 * | 10/2001 | Kirwan, Jr. | ........ | A61B 18/1402 29/825 |
| 6,800,077 B1 * | 10/2004 | Mucko | ............... | A61B 18/1442 606/51 |
| 6,860,882 B2 * | 3/2005 | Battles | ............... | A61B 18/1442 606/51 |

* cited by examiner

*Primary Examiner* — Ronald Hupczey, Jr.
(74) *Attorney, Agent, or Firm* — Troutman Pepper Hamilton Sanders LLP

(57) ABSTRACT

An electro-surgical bipolar forceps includes a first tip and a second tip, each having a body. The body has a distal end and a proximal end. The body has a first groove having a substantially planar base proximate the proximal end. A substantially planar face is proximate to the distal end of the tip body. The base and the face on each tip define planes that are approximately perpendicular with respect to each other. A tip assembly includes a tip and an engagement plug. When making the tip assembly, a planar surface on the engagement plug is aligned with the planar base of the groove in the tip. Then the tip is connected to the engagement plug.

29 Claims, 4 Drawing Sheets

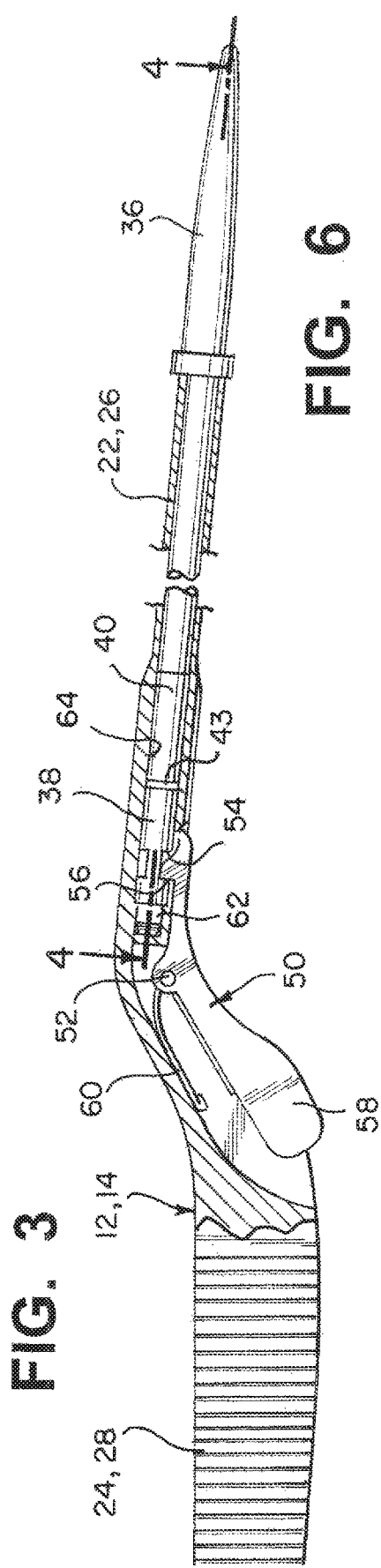
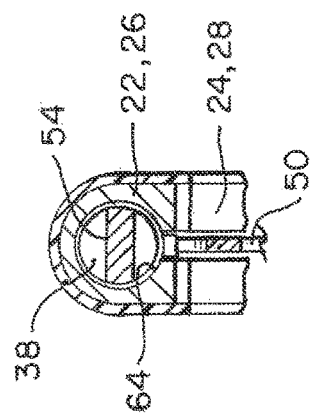
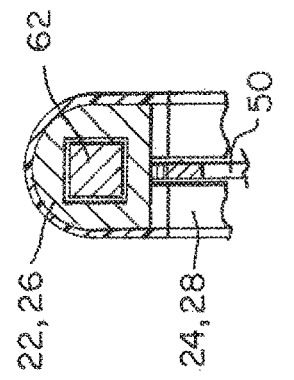
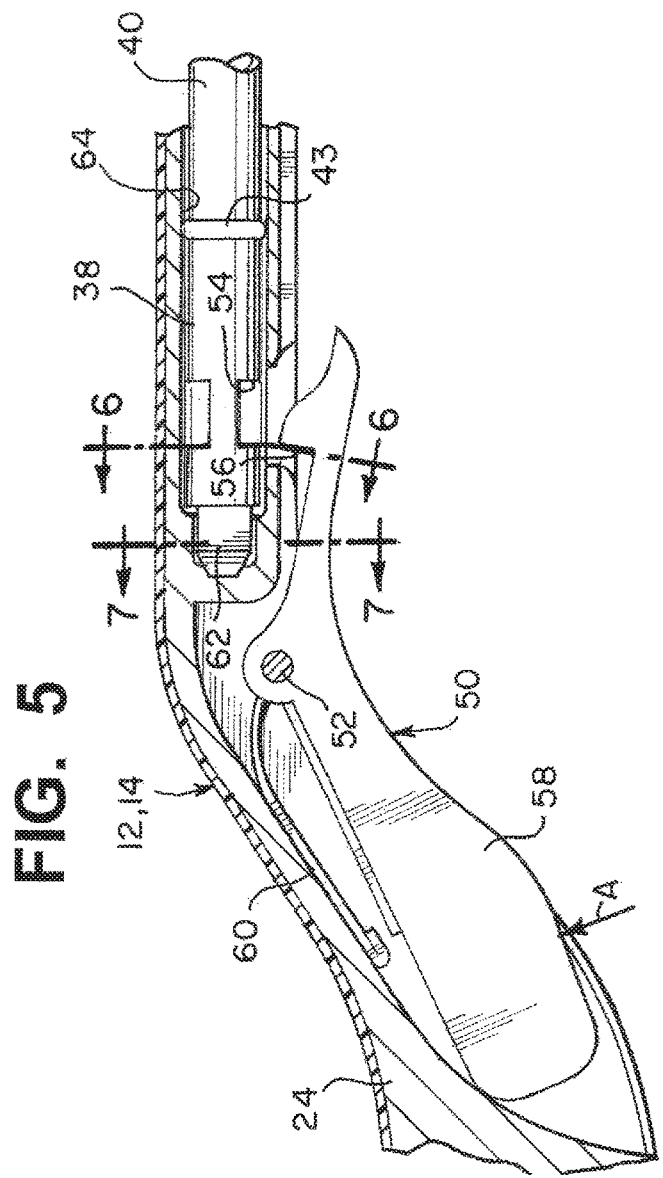

ELECTRO-SURGICAL BIPOLAR FORCEPS

CROSS REFERENCE TO RELATED PCT APPLICATION

This application is a continuation of U.S. patent application Ser. No. 11/772,969, filed Jul. 3, 2007.

BACKGROUND OF THE INVENTION

1. Field of the Invention

The present invention relates to an electro-surgical bipolar forceps, and more particularly, to electro-surgical bipolar forceps that have replaceable tip assemblies.

2. Discussion of Related Art

Electro-surgical bipolar forceps are known in the art, and are commonly used in surgical procedures to grasp, dissect, seal and clamp tissue. Bipolar forceps comprise a pair of tips, and each tip comprises an electrode in communication with a source of electrical power. In most cases, the tips are fixedly attached to the handles. Therefore, to reuse these types of bipolar forceps, the bipolar forceps must be sterilized between each use. In addition, after multiple uses the tips of the forceps often become misaligned thereby requiring returning the forceps to the manufacturer for realignment, if possible.

U.S. Pat. No. 6,050,996 to Schmaltz et al. discloses a bipolar electro-surgical instrument that has replaceable electrodes. But these replaceable electrodes do not permit the tip assembly to vary in shape and size. In addition, these replaceable electrodes do not address the problem of correcting misaligned jaws. Accordingly, there is still a need in the art for electro-surgical bipolar forceps that have replaceable tip assemblies. Thus, the tips would no longer be subject to a sterilization process as they can simply be disposed of and replaced with a new pair of tips. In addition, the new tip assembly includes at least one groove in a proximal end of a tip to aid in the manufacturing process to ensure that the distal portion (or face at the distal end) of the tip assembly will automatically align in the proper orientation with a mating distal portion of the other tip assembly in the bipolar electro-surgical instrument.

SUMMARY OF THE INVENTION

In accordance with an exemplary embodiment, the present invention includes a tip for use with an electro-surgical medical device. The tip has a body. The body has a distal end and a proximal end. The body has a first groove having a substantially planar base proximate the proximal end. A substantially planar face is proximate to the distal end of the tip body. The base and the face on the tip define planes that are approximately perpendicular with respect to each other.

In accordance with another exemplary embodiment, the present invention includes an electro-surgical bipolar forceps includes a first tip and a second tip, each having a body. The body has a distal end and a proximal end. The body has a first groove having a substantially planar base proximate the proximal end. A substantially planar face is proximate to the distal end of the tip body. The base and the face on each tip define planes that are approximately perpendicular with respect to each other.

In accordance with other exemplary embodiment, the present invention includes a tip assembly, which includes a tip and an engagement plug. When making the tip assembly, a planar surface on the engagement plug is aligned with a planar base of a groove in the tip. Then the tip is connected to the engagement plug.

BRIEF DESCRIPTION OF THE DRAWINGS

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components, and wherein:

FIG. 3 is a partial cross-sectional view of the tip assembly and insert tube of the electro-surgical bipolar forceps of FIG. 1;

FIG. 5 is a partial cross-sectional view showing the tip assembly being selectively engaged with the insert tube;

FIG. 6 is a cross-sectional view taken along line 6-6 of FIG. 5 and looking in the direction of the arrows;

FIG. 7 is a cross-sectional view taken along line 6-6 of FIG. 5 and looking in the direction of the arrows;

DETAILED DESCRIPTION OF THE CURRENTLY PREFERRED EXEMPLARY EMBODIMENT

Figure 1:
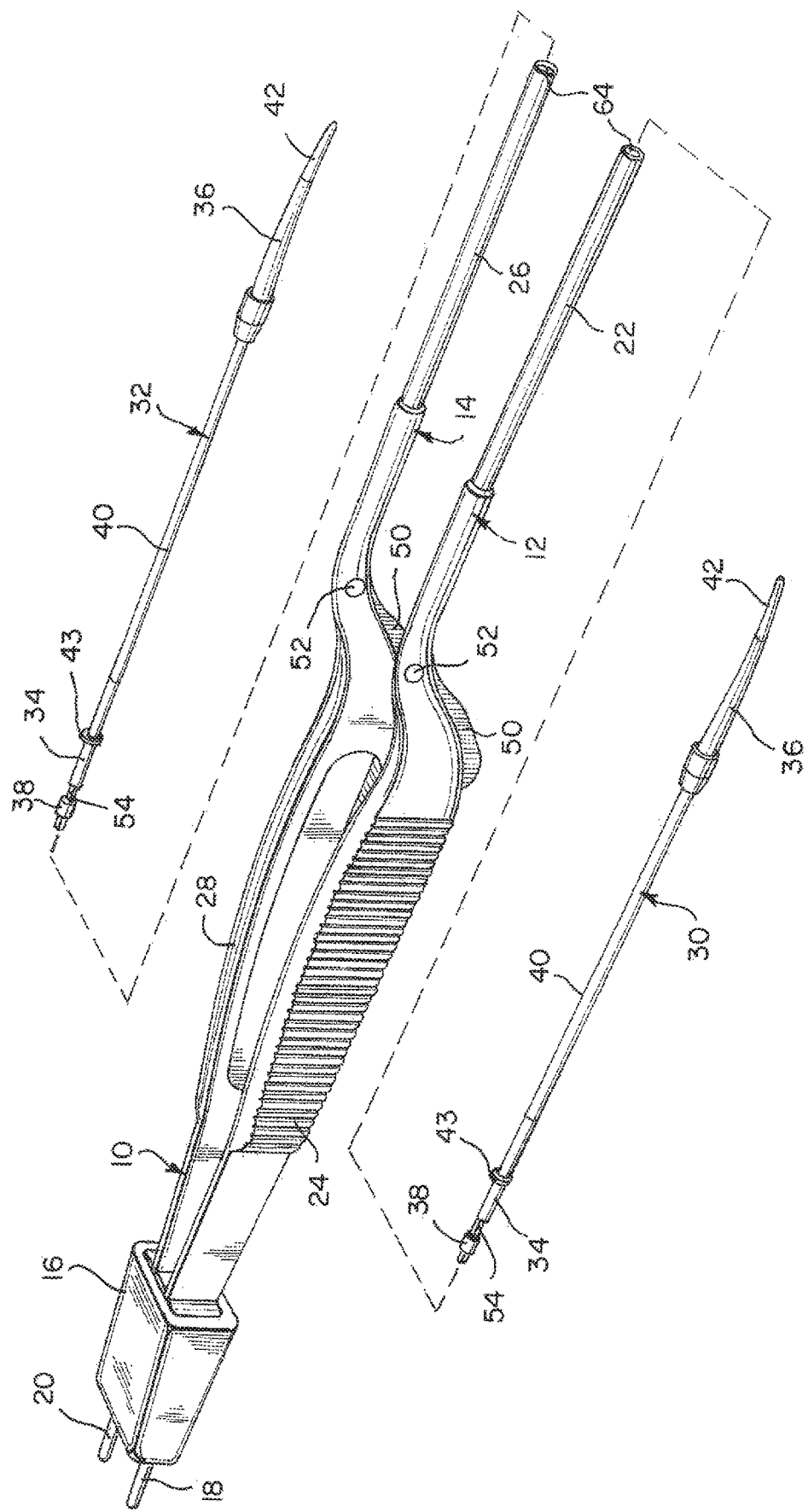
FIG. 1 is an exploded perspective view of the electro-surgical bipolar forceps in accordance with the present invention.
Figure 2:
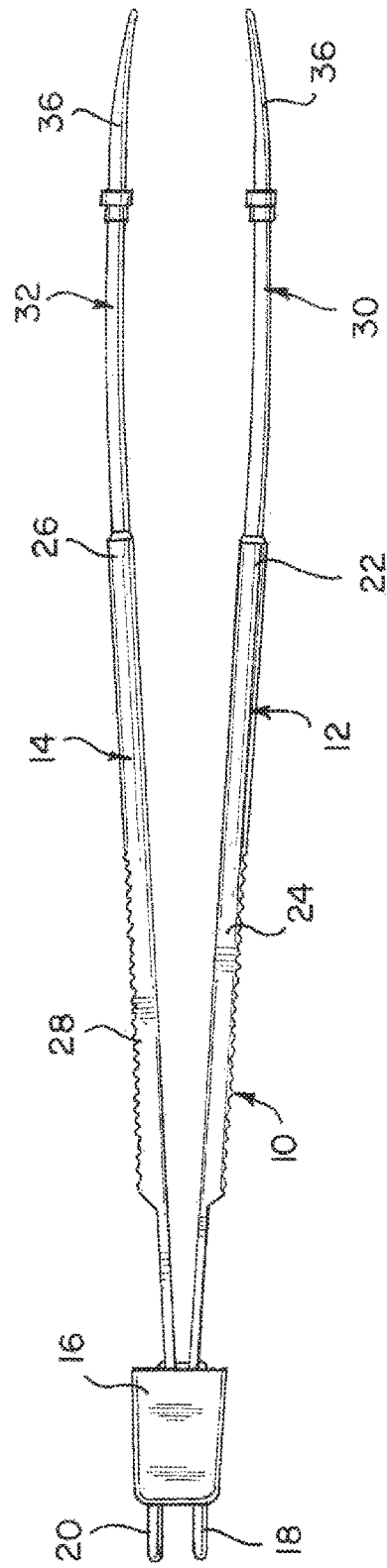
FIG. 2 is a top view of the electro-surgical bipolar forceps of FIG. 1.

Referring now to FIGS. 1 though 10, an electro-surgical bipolar forceps 10, in accordance with the present invention, is illustrated. Forceps 10 include a first member 12 and a second member 14, which are connected together by a connector 16. Each member 12, 14 is electrically insulated from the other member within connector housing 16 and is connected to a corresponding contact pin 18, 20. Contact pins 18, 20 are configured to be connected to a power source, in a manner known to those skilled in the art. First member 12 has a first insert tube 22 disposed at a distal end thereof and a handle 24 disposed at a proximal end thereof. Likewise, second member 14 has a second insert tube 26 disposed at a distal end thereof and a handle 28 disposed at a proximal end thereof.

Insert tubes 22, 26 are illustrated as being cylindrical in shape, but are not to be limited to this shape. Of course, insert tubes 22, 26 can be of other closed or even open shapes, such as, for example, square, rectangular, and other polygonal or other irregular shapes.

Figure 10:
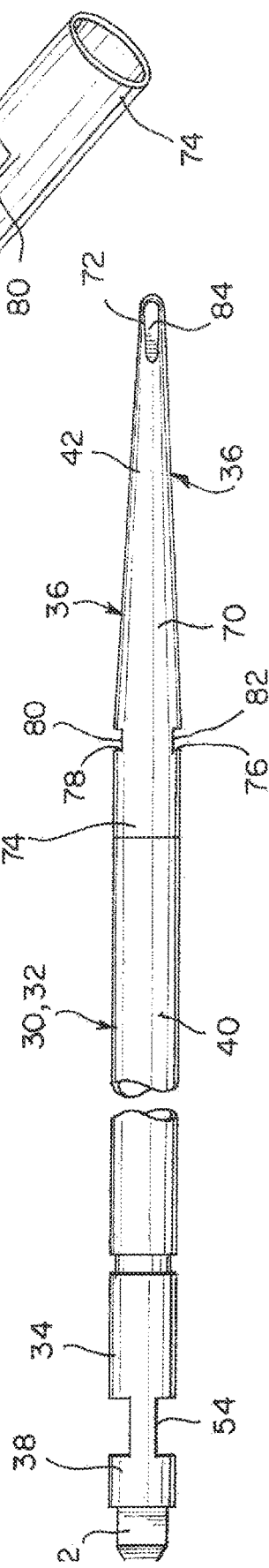
FIG. 10 is a side view of the tip assembly.

Forceps 10 also include a first tip assembly 30 that is selectively engageable with either first insert tube 22 or second insert tube 26 (in the illustration, first tip assembly 30 is shown selectively engaged with the first insert tube 22). A second tip assembly 32 is selectively engageable either with first insert tube 22 or second insert tube 26. Each tip assembly 30, 32 has a proximal end 34 and a distal end 36, as illustrated in FIGS. 1 and 10. The proximal end of the tip assembly is preferably selectively engageable with either insert tube 22, 26. Each tip assembly 30, 32 include an engagement plug 38, an oversheath sleeve 40, an electrically conductive tip 42, and a distal seal 43. In addition, as disclosed in U.S. Pat. Nos. 6,929,645 and 6,860,882, the disclosures of which are hereby incorporated by reference in their entirety, each tip assembly may include a spacer sleeve so that the length of the tip assembly can vary. Further, the shapes of the tips can vary depending upon the needs of the surgeon. Additionally, a heat pipe is preferably disposed within the oversheath sleeve 40 and between the engagement plug 38 and tip 36. Heat pipe is totally enclosed in sealed chamber and is effective to remove heat from the tip 42. The use of a heat pipe in bipolar forceps is known from the teaching of U.S. Pat. Nos. 6,929,645, 6,860,882, 6,074,389 and 6,206,876, the disclosures of these patents are each hereby incorporated by reference in their entirety.

Each member 12, 14 includes a release button 50 that is connected to insert tube 22, 26 by a pivot pin connection 52. As illustrated in FIGS. 3, 5 and 10, engagement plug 38 has a recess 54. Recess 54 is shaped to receive a locking shoulder 56 disposed at one end of the release button 50. Release button 50 has a release tab 58 disposed at an opposite end from locking shoulder 56. A spring 60 is connected to member 12, 14 at one end and to release button 50 at an opposite end. Spring 60 normally biases releases button 50 into the locked position shown in FIG. 3. The release button is moveable from the locked position to the unlocked position by the application of an external force in the direction indicated by arrow A in FIG. 5. For example, a surgeon may depress release tab 58 in the direction indicated by arrow A to thereby move locking shoulder 56 away from recess 54 in the engagement plug 38. Once release tab 58 is sufficiently depressed, the surgeon may thereafter grasp the tip assembly and remove the entire tip assembly 30, 32 from the respective insert tube 22, 26. During insertion of a tip assembly 30, 32 into the respective insert tube 22, 26, the operator can manually insert the tip assembly 30, 32 such that the proximal end, or engagement plug 38, is received within the insert tube 22, 26. The extreme end 62 of engagement plug 38 may have a keyed shape in cross-section, such as a square as shown in FIG. 7, to be matingly received within a correspondingly-shaped socket within the insert tube to ensure that the tip assembly is aligned in the proper orientation with respect to the other tip assembly. Thus, extreme end 62 has four planar surfaces.

Figure 8:
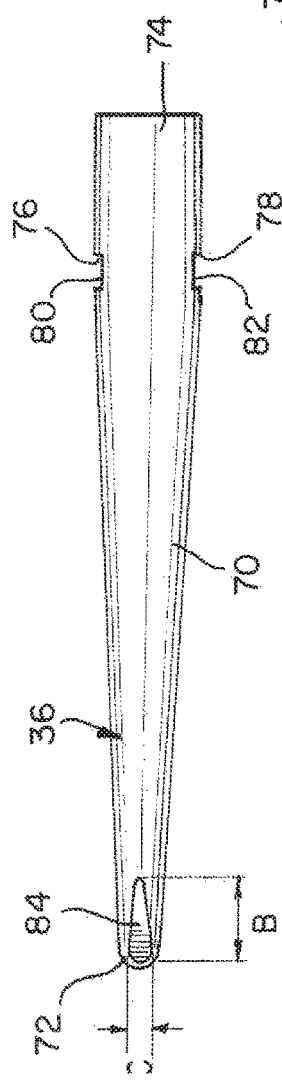
FIG. 8 is a side view of the tip.
Figure 9:
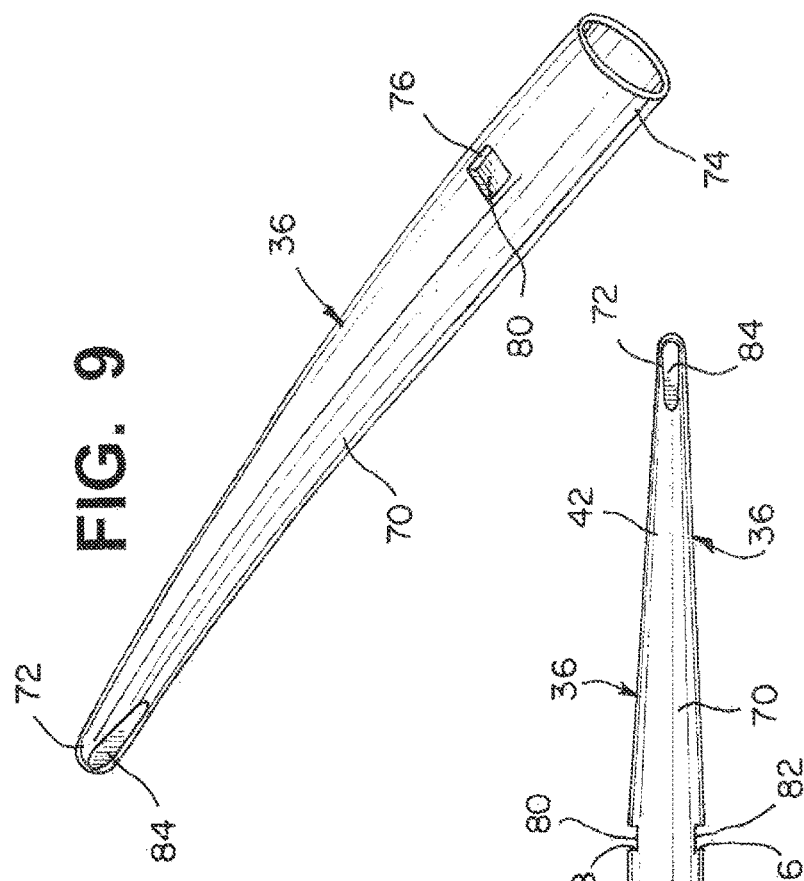
FIG. 9 is a perspective view of the tip.

Referring now to FIGS. 8-10, each tip 36 has an elongated body 70 having a distal end 72 and a proximal end 74. Body 70 has a first groove 76 and a second groove 78, each being disposed proximate to proximal end 74. Each groove 76, 78 has a substantially planar base 80, 82, respectively. Each groove 76, 78 preferably has an approximately rectangular shape in cross-section, as shown in FIGS. 8 and 10. Body 70 has a substantially planar face 84 proximate distal end 72. Tip body 70 extends axially from proximal end 74 to distal end 72. In a currently preferred exemplary embodiment grooves 76, 78 are disposed in approximately the same axial position along body 70, as shown in FIG. 8. Bases 80, 82 and face 84 define planes that are approximately perpendicular with respect to each other. In a currently preferred exemplary embodiment, face 84 has a length B of no greater than about 0.09 in and a width C of no greater than about 0.05 in. By using the software UNIGRAPHICS®, which is commercially available from Unigraphics Solutions Inc. of Cypress, Calif., one skilled in the art can calculate that face 84 has a surface area of no greater than about 0.004 inches$^2$.

In a currently preferred exemplary embodiment, to manufacture the tip assembly 30, 32, rectangular grooves 76, 78 are used as positional geometry in the fixturing process to provide positive alignment features, which result in repeatability due to assembling off of two flat surfaces rather than one. In contrast, in conventional assembly processes, manufacturers may fixture off of the tip face 84, which adds potential for damages to be incurred at the tip's coagulating surface that can result in impaired performance during use and a diminished surface finish. Grooves 76, 78 are thus used to fix the position of tip 36, and face 84 may then be machined to be precisely perpendicular to the planar base surfaces 80, 82, of grooves 76, 78, respectively. Tip 36 is then connected to oversheath sleeve 40, which optionally contains a heat pipe, by using grooves 76, 78 to once again fix the position of tip 36. Thereafter, the connected tip and sleeve are held by grooves 76, 78 and are connected to engagement plug 38 such that the planar surfaces of extreme end 62 are aligned precisely perpendicular to two of the four planar surfaces and, of course, parallel to the other two of the four planar surfaces. Thus, when the tip assemblies are inserted in the handle's insert tubes 22, 26, in the closed position, the face 84 of the one tip body mates with the face 84 of the other tip body with essentially no overlap, despite the relatively small dimensions of face 84. In other words, the faces 84 essentially align perfectly with one another.

Figure 4:
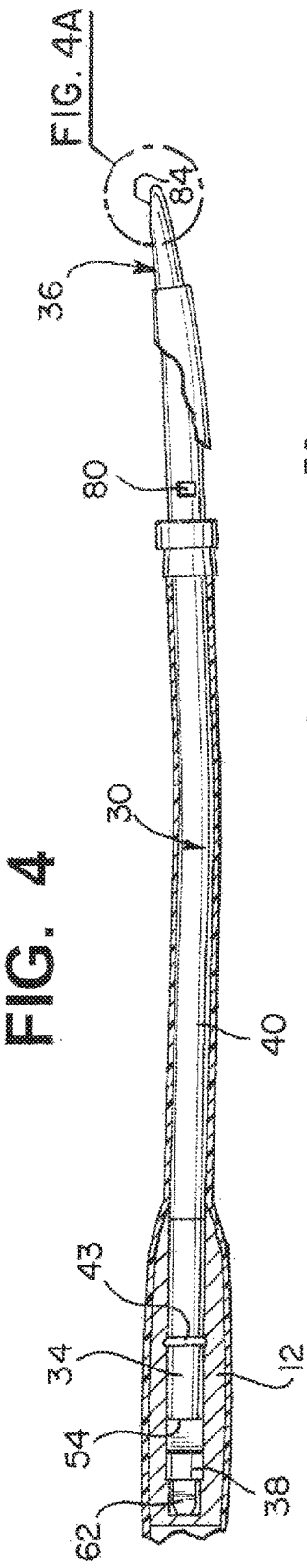
FIG. 4 is a cross-sectional view of the tip assembly taken along line 4-4 of FIG. 3 and looking in the direction of the arrows.
Figure 4A:
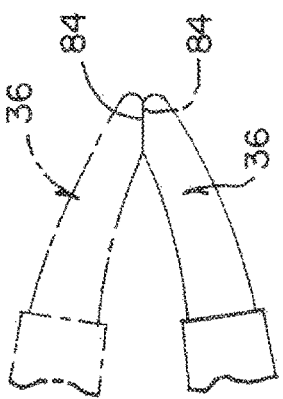
FIG. 4A is an enlarged partial top view showing the circle labeled as FIG. 4A in FIG. 4, and showing the bipolar forceps in the closed position.

As shown in FIGS. 1, 4 and 4A, release tab 58 is disposed on a "lower" end of the forceps 10. Thus, during use, a surgeon can look down the "upper" portion of the forceps with an unobstructed view of the surgical site. This is especially true with the relatively small faces 84 of tips 36 in accordance with the present invention. Such a geometry provides precision to the surgeon through visualization. The contoured design of the tip body also permits a surgeon to glide along delicate anatomy such as arteries, nerves and other delicate tissue.

Each insert tube 12, 14 has an inner surface 64. Inner surface 64 is preferably covered or coated with an electrically insulated material. Thereafter, a portion of that coating or covering is removed at the distal end of the inner surface of the insert tube so that this portion of the inner surface of the insert tube is electrically conductive. The electrically conductive inner surface portion of the insert tube, in a selectively engaged position of the tip assembly within the insert tube, is located distally with respect to a proximal seal. Thus, only the predetermined portion of the inner surface of the insert tube has the insulating material removed therefrom.

The current path from contact pins 18, 20 to the tips 36 extends from pin 18, 20, through the handle 24, 28 (of course, the outer portion of the handle, insert tube and most of the tip assembly can be covered with an insulating material to electrically isolate the member and tip assemblies from each other and from the user), to the insert tube 22, 26, to the oversheath sleeve 40 where they contact the insert tube in the predetermined area, to the heat pipe 46 to the tip 36. Tips 36 are preferably made of copper and coated with gold or other biocompatible material. In use, fluid may collect in and around button 50 and on the proximal side of engagement plug 38 with respect to the proximal seal, but because all of these surfaces are insulated, there is no or at least very minimal risk of an electrical short. The handles are preferably made of stainless steel or titanium. The tip assembly includes engagement plug 38 that is preferably made of cooper or plastic. Oversheath sleeve and spacer sleeve are preferably made of stainless steel or titanium. Proximal and distal seals are preferably made of silicone.

Having described the presently preferred exemplary embodiment of an electro-surgical bipolar forceps in accordance with the present invention, it is believed that other modifications, variations and changes will be suggested to those skilled in the art in view of the teachings set forth herein. It is, therefore, to be understood that all such modifications, variations, and changes are believed to fall within the scope of the present invention as defined by the appended claims. All publications and references cited herein are expressly incorporated herein by reference in their entirety.

What is claimed:

1. A tip assembly for use with an electro-surgical medical device, said tip comprising:
    a tip comprising a body comprising a distal end and a proximal end, a first groove proximate said proximal end comprising a substantially planar base, a substantially planar face proximate said distal end, and an engagement plug comprising a recess proximal of said first groove and spaced entirely from said proximal end,
    an oversheath sleeve connected intermediate the engagement plug and the tip, and
    a release button comprising a locking shoulder configured to engage the recess of the engagement plug;
    wherein said base and said planar face define planes that are approximately perpendicular with respect to each other, said first groove being disposed between said recess and said planar face.

2. A tip assembly according to claim 1, wherein said first groove is approximately rectangular in cross-section.

3. A tip assembly according to claim 2, wherein said body is elongated.

4. A tip assembly according to claim 3, wherein said body is made of an electrically conductive material.

5. A tip assembly according to claim 1, wherein said body has a second groove proximate said proximal end.

6. A tip assembly according to claim 5, wherein said second groove is approximately rectangular in cross-section.

7. A tip assembly according to claim 6, wherein said second groove has a substantially planar base, wherein said base of said second groove and said face define planes that are approximately perpendicular with respect to each other.

8. A tip assembly according to claim 7, wherein said body is elongated.

9. A tip assembly according to claim 8, wherein said body is made of an electrically conductive material.

10. The tip according to claim 5, wherein said tip body extending axially from said proximal end to said distal end, said first groove and said second groove being disposed in approximately the same axial position along said body.

11. An electro-surgical bipolar forceps comprising:
    a first tip comprising a body, said body comprising a distal end and a proximal end, a first groove proximate said proximal end and having a substantially planar base, a substantially planar face proximate said distal end, and an engagement plug comprising a recess proximal of said first groove and spaced entirely from said proximal end;
    an oversheath sleeve connected intermediate the engagement plug and the tip; and
    a release button comprising a locking shoulder configured to engage the recess of the engagement plug;
    wherein said base and said planar face define planes that are approximately perpendicular with respect to each other, said first groove being disposed between said recess and said planar face.

12. The electro-surgical bipolar forceps according to claim 11, further comprising a second tip having a body, said second tip body having a distal end and a proximal end, said second tip body having a first groove proximate said proximal end, said first groove of said second tip body having a substantially planar base, said second tip body having a substantially planar face proximate said distal end; and wherein said base and said face of said second tip body define planes that are approximately perpendicular with respect to each other.

13. The electro-surgical bipolar forceps according to claim 12, wherein said first groove in each of said first tip and said second tip is approximately rectangular in cross-section.

14. The electro-surgical bipolar forceps according to claim 13, wherein said body of said first tip is elongated, and said body of said second tip is elongated.

15. The electro-surgical bipolar forceps according to claim 14, wherein said body of said first tip is made of an electrically conductive material, and said body of said second tip is made of an electrically conductive material.

16. The electro-surgical bipolar forceps according to claim 12, wherein said first tip body has a second groove proximate said proximal end, and said second tip body has a second groove proximate said proximal end.

17. The electro-surgical bipolar forceps according to claim 16, wherein said second groove in each of said first tip and said second tip is approximately rectangular in cross-section.

18. The electro-surgical bipolar forceps according to claim 17, wherein said second groove in said first tip has a substantially planar base, wherein said base of said second groove in first tip and said face in said first tip define planes that are approximately perpendicular with respect to each other, and said second groove in said second tip has a substantially planar base, wherein said base of said second groove in second tip and said face in said second tip define planes that are approximately perpendicular with respect to each other.

19. The electro-surgical bipolar forceps according to claim 18, wherein said body of said first tip is elongated, and said body of said second tip is elongated.

20. The electro-surgical bipolar forceps according to claim 19, wherein said body of said first tip is made of an electrically conductive material, and said body of said second tip is made of an electrically conductive material.

21. The electro-surgical bipolar forceps of claim 16, wherein said first tip body extending axially from said proximal end to said distal end, said first groove and said second groove in said first tip body being disposed in approximately the same axial position along said first tip body, said second tip body extending axially from said proximal end to said distal end, said first groove and said second groove in said second tip body being disposed in approximately the same axial position along said second tip body.

22. The electro-surgical bipolar forceps according to claim 12, wherein in the closed position, the face of the first tip body mates with the face of said second tip body with essentially no overlap.

23. The electro-surgical bipolar forceps of claim 22, wherein the face has a surface area of no greater than about 0.004 in$^2$.

24. The electro-surgical bipolar forceps of claim 22, wherein the face has a length of no greater than about 0.09 inches and a width of no greater than about 0.05 inches.

25. A method of assembling a multi-part tip assembly for use in an electro-surgical medical device, said multi-part tip comprising:
- an engagement plug and a tip, said tip having a body having a distal end and a proximal end,
- said body having a first groove proximate said proximal end comprising a substantially planar base, and a substantially planar face proximate said distal end,
- said engagement plug proximal of said first groove and comprising a recess spaced entirely from said proximal end,
- an oversheath sleeve connected intermediate the engagement plug and the tip, and
- a release button comprising a locking shoulder configured to engage the recess of the engagement plug,
- wherein said method comprising the steps of:
- aligning the planar surface of the recess of the engagement plug with the first groove planar base surface; and
- connecting the tip to the engagement plug.

26. A method of manufacturing a tip for use in an electro-surgical medical device, said tip comprising a body comprising a distal end and a proximal end, said body having a first groove proximate said proximal end, said first groove having a substantially planar base, an engagement plug proximal of said first groove comprising a recess spaced entirely from said proximal end, an oversheath sleeve connected intermediate the engagement plug and the tip, and a release button comprising a locking shoulder configured to engage the recess of the engagement plug;
- wherein said method comprising the steps of:
- maintaining the position of the tip body by grasping the planar base of the first groove; and
- machining a substantially planar face in said tip body proximate its distal end while the position of said tip body is being maintained.

27. The method according to claim 26, wherein in said machining step, said planar face and said planar base define planes that are approximately perpendicular with respect to each other.

28. A method of manufacturing a tip for use in an electro-surgical medical device, said tip comprising a body comprising a distal end and a proximal end, said body comprising a first groove and a second groove proximate said proximal end each comprising a substantially planar base, and an engagement plug proximal of said first groove and comprising a recess spaced entirely from said proximal end,
- an oversheath sleeve connected intermediate the engagement plug and the tip, and
- a release button comprising a locking shoulder configured to engage the recess of the engagement plug;
- wherein said base and said planar face define planes that are approximately perpendicular with respect to each other, said first groove being disposed between said recess and said planar face,
- wherein said method comprising the steps of:
- maintaining the position of the tip body by grasping the planar base of the first groove and the planar base of the second groove; and
- machining a substantially planar face in said tip body proximate its distal end while the position of said tip body is being maintained.

29. The method according to claim 28, wherein in said machining step, said planar face and said planar base of the first groove define planes that are approximately perpendicular with respect to each other, and said planar face and said planar base of the second groove define planes that are approximately perpendicular with respect to each other.

* * * * *